United States Patent [19]

Chodnekar et al.

[11] 4,059,600
[45] Nov. 22, 1977

[54] EPOXY DODECADIENAMIDES

[75] Inventors: Madhukar Subraya Chodnekar, Basel; Albert Pfiffner, Pfaffhausen; Norbert Rigassi, Arlesheim; Ulrich Schwieter, Reinach; Milos Suchy, Pfaffhausen, all of Switzerland

[73] Assignee: Hoffmann-La Roche, Inc., Nutley, N.J.

[21] Appl. No.: 216,256

[22] Filed: Jan. 7, 1972

[30] Foreign Application Priority Data

Jan. 20, 1971 Switzerland .................... 849/71
Dec. 15, 1971 South Africa ................ 71/8418
Dec. 15, 1971 New Zealand .................. 165805

[51] Int. Cl.$^2$ ............... C07D 303/46; C07D 303/40; C07D 303/28; A01N 9/28
[52] U.S. Cl. .................... 260/348.46; 260/348.61; 260/348.57; 260/404; 260/410.9 R; 260/410.9 N; 260/413; 260/601 R; 260/614 R; 260/632 R; 424/278; 424/314; 424/320; 424/342
[58] Field of Search ............... 260/410.9 R, 410.9 N, 260/348 A, 413

[56] References Cited

U.S. PATENT DOCUMENTS

| 2,951,853 | 9/1960 | Matsui .................... 260/347.5 |
| 3,716,565 | 2/1973 | Henrick et al. ............ 260/410.9 R |
| 3,752,843 | 8/1973 | Henrick .................... 260/465.9 |
| 3,793,353 | 2/1974 | Henrick .................... 260/405 |
| 3,904,662 | 9/1975 | Henrick et al. ............ 260/410 |

OTHER PUBLICATIONS

Wiley et al., J. Am. Chem. Soc. 79, pp. 2266–2271 (1957).

*Primary Examiner*—Donald G. Daus
*Assistant Examiner*—Diana G. Rivers
*Attorney, Agent, or Firm*—Samuel L. Welt; Bernard S. Leon; William H. Epstein

[57] ABSTRACT

Ethers, esters and amides of dodeca-2,4-dien 1-ols or 1-oic acids which have a methyl or ethyl side chain at the 11-position which are useful in killing and preventing proliferation of insects, by upsetting their hormone balance and a process for preparing these ethers, esters and amides including intermediates in this process.

3 Claims, No Drawings

EPOXY DODECADIENAMIDES

BRIEF SUMMARY OF THE INVENTION

This invention is directed to compounds of the formula

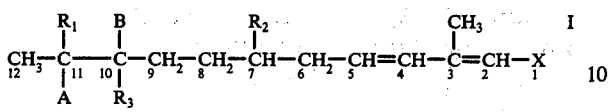

wherein $R_1$ and $R_2$ are methyl or ethyl; $R_3$ is hydrogen, or methyl; A and B are individually hydrogen or taken together form a carbon to carbon bond or an oxygen bridge and X is -COOR, -CH$_2$OR or

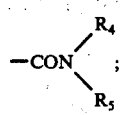

R is lower alkyl, lower alkenyl or lower alkynyl; and $R_4$ and $R_5$ are hydrogen or lower alkyl
which are useful in upsetting the hormone balance of pests to prevent them from growing and reproducing.

DETAILED DESCRIPTION OF THE INVENTION

As used throughout the application, the term "lower alkyl" comprehends both straight and branched chain saturated hydrocarbon groups containing from 1 to 6 carbon atoms such as methyl, ethyl, propyl, isopropyl, etc. The term "lower alkoxy" comprehends lower alkoxy groups containing from 1 to 6 carbon atoms such as methoxy, propoxy, ethoxy, etc., preferably methoxy. The term "halogen" as used throughout the application includes all four halogens, i.e., bromine, chlorine, fluorine and iodine. The term "lower alkanoyl" includes lower alkanoyl groups containing from 1 to 6 carbon atoms such as acetyl, propionyl, formyl, butyryl, etc. The terms "lower alkenyl" and "lower alkynyl" includes both straight chain and branched chain hydrocarbon groups containing 2 to 6 carbon atoms such as vinyl, allyl, butenyl, pentenyl, ethynyl, propargyl, butynyl, etc.

The term "dilower alkylamino" as used throughout the application includes dilower alkylamino groups wherein the lower alkyl moieties contain from 1 to 6 carbon atoms such as methyl, ethyl, isopropyl, etc. The term "dilower alkylamino lower alkyl" as used throughout the application includes dilower alkylamino lower alkyl groups wherein the lower alkyl moieties are defined as above.

The term "aryl" as used throughout the application includes mono-nuclear aryl groups such as phenyl which can be unsubstituted or substituted in one or more positions with a lower alkyl, halogen, an electron donating group, lower alkoxy, amino, nitro, mono- and di-lower alkylamino, etc., or polynuclear aryl groups such as naphthyl, anthryl, phenanthryl, azulyl, etc. which may be unsubstituted or substituted with one or more of the aforementioned groups. The term "aryloxy" comprehends aryloxy groups wherein the aryl moiety is defined as above. The preferred aryloxy group is phenoxy.

The compounds of formula I are useful in the control of pests such as *Tenebrio molitor* (yellow mealworm), *Tineola biselliella* (clothes moth), *Esphestia Kuhniella*, *Dysdercus cingulatus*, *Carpocapsa pomonella* (codling moth), *Leptinotarsa decemlineata* (Colorado beetle), *Calandra granaria* (grain weevil), etc.

In contrast to most of the known pest-control agents which kill, disable or repell the pests by acting as contact-poisons and feed-poisons, the compound of formula I above prevents maturation and proliferation of these pests by interfering with their hormonal system. In insects, for example, the transformation into the imago, the laying of eggs capable of development and the development of laid normal eggs, is disturbed. Furthermore, the sequence of generations is interrupted and the insects are indirectly killed.

The compounds of formula I above are practically non-toxic to vertebrates. The toxicity of these compounds is greater than 2,500 mg/kg body weight. Moreover, these compounds are readily degraded and the risk of accumulation is therefore excluded. Therefore, these compounds can be used without fear of danger in the control of pests in animals; plants; foods; and textiles.

Generally, in controlling invertebrate animals, the compounds of formula I above thereof are applied such as by spray to the material to be protected, e.g., foodstuffs, feeds, textiles, plants in an amount of from about 0.01 percent to 0.5 percent by weight of the material to be protected. Generally, it is preferred to utilize the compounds of formula I above in a composition with a suitable inert carrier. Any conventional inert carrier can be utilized. The composition which contains an effective amount of the compounds of formula I above should be applied to the material to be protected to provide a concentration of from about 0.01 percent to 0.1 percent of the compound of formula I above on said material. In controlling parasites, it is generally preferred to apply from about $10^{-3}$ to about $10^{-6}$ grams of the compound of formula I per cm$^2$ of the surface of the material to be protected.

The compound of formula I can, for example, be used in the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them by the action of external influences (e.g., contact with moisture) or in the animal body itself.

The compound of formula I above can be used as solutions suitable for spraying on the material to be protected which can be prepared by dissolving or dispersing these compounds in a solvent such as mineral oil fractions; cold tar oils; oils of vegetable or animal origins; hydrocarbons such as naphthalenes; ketones such as methyl ethyl ketone; or chlorinated hydrocarbons such as tetrachloroethylene, tetrachlorobenzene, and the like. The compounds of formula I above can also be prepared in forms suitable for dilution with water to form aqueous liquids such as, for example, emulsion concentrates, pastes or powders. The compounds of formula I above can be combined with solid carriers for making dusting or strewing powders as, for example, talc, kaolin, bentonite, calcium carbonate, calcium phosphate, etc. The compositions containing the compound of formula I above can contain, if desired, emulsifiers, dispersing agents, wetting agents, or other active substances such as fungicides, bacteriacides, nematocides, fertilizers and the like.

The compound of formula I can be prepared by a. reacting a carbonyl of the formula:

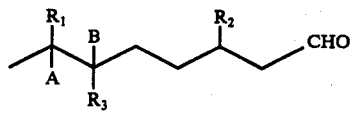

(II)

wherein $R_1$, $R_2$, $R_3$, A and B are as above; with a phosphine oxide of the general formula:

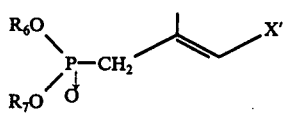

(III)

wherein X' is —COOR or

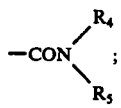

R, $R_4$ and $R_5$ are as above; and $R_6$ and $R_7$ are each lower alkyl or aryl; or b. reacting a compound of the general formula:

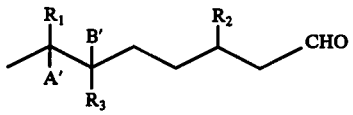

(II-A)

wherein $R_1$, $R_2$ and $R_3$ have the significance given earlier and A' and B' are individually hydrogen or taken together form a carbon to carbon bond
with a phosphorane of the general formula:

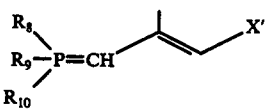

(IV)

wherein X' is as above; and $R_8$, $R_9$ and $R_{10}$ are aryl or dialkylamino; or c. reacting a carbonyl compound of the general formula:

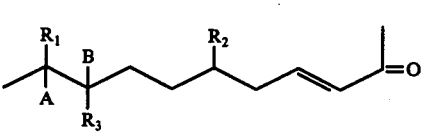

(V)

wherein $R_1$, $R_2$, $R_3$, A and B are as above; with a phosphine oxide of the general formula:

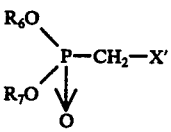

(VI)

wherein $R_6$, $R_7$ and X' are as above;

d. reacting a compound of the general formula:

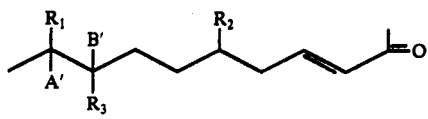

(VII)

wherein $R_1$, $R_2$, $R_3$, A' and B' are as above; with a phosphorane of the general formula:

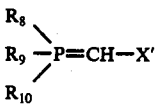

(VIII)

wherein $R_8$, $R_9$, $R_{10}$ and X' are as above;

e. reacting a compound of the general formula:

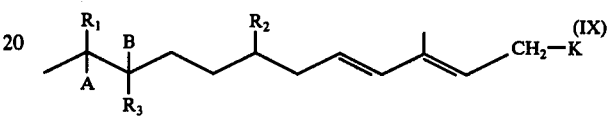

(IX)

with a compound of the general formula:

J—R     (X)

wherein in formulae IX and X, R, $R_1$, $R_2$, $R_3$, A and B are as above; and one of K and J is chlorine, bromine or iodine, and the other is hydroxyl; or f. epoxidizing a polyene compound of the formula:

I-A wherein $R_1$, $R_2$, $R_3$, and X are as above; to produce a compound of the formula:

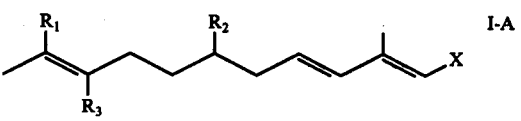

I-B wherein $R_1$, $R_2$, $R_3$ and X are as above; or g. converting an acid of the formula:

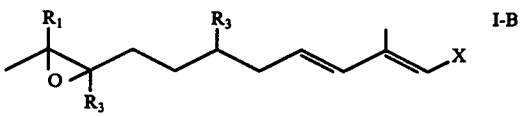

XI wherein A, B, $R_1$, $R_2$ and $R_3$ are as above; to a lower alkyl, lower alkenyl or lower alkynyl ester, or to an amide or di or mono lower alkyl substituted amide; or h. re-esterifying a compound of the formula:

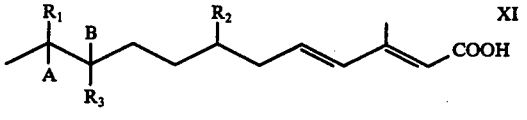

I-C wherein R, $R_1$, $R_2$, $R_3$, A and B are as above; or i. converting a compound of the formula I-C to a compound of the formula:

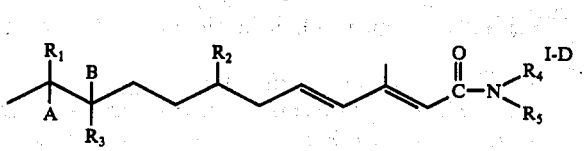

wherein A, B, $R_1$, $R_2$, $R_3$, $R_4$ and $R_5$ are as above.

The phosphine oxides of formulae III and VI can carry alkoxy or aryloxy groups. The aryl groups denoted by $R_6$ and $R_7$ can be mono or polynuclear, substituted or unsubstituted aryl groups. Of the alkoxy groups, those containing from 1 to 4 carbon atoms (e.g., methoxy, ethoxy or isopropoxy) are preferred. Of the aryloxy groups, especially preferred are phenoxy groups which can be mono or polysubstituted by various substituents such as, for example, alkyl, alkoxy, halogen, dialkylamino and nitro.

In the phosphoranes of formulae IV and VIII, which can be obtained from the corresponding phosphonium salts, $R_8$, $R_9$ and $R_{10}$ can be an aryl or dialkylamino group. The aryl groups denoted by $R_8$, $R_9$ and $R_{10}$ include all generally known aryl groups; for example, mononuclear groups such as phenyl and substituted phenyl such as, for example, tolyl, xylyl, mesityl and p-methoxyphenyl, as well as polynuclear groups such as, for example, naphthyl, anthryl, phenanthryl, azulyl, etc. The dialkylamino groups denoted by $R_8$, $R_9$, $R_{10}$ are preferably dialkylamino groups containing from 1 to 4 carbon atoms in each of the alkyl groups such as, for example, dimethyl, diethyl or diisopropylamino.

Preferred polyene compounds of formula I are those in which R is methyl, ethyl, 3-pentyl, allyl or propargyl groups. Polyene compounds of formula I in which A and B together represent a carbon to carbon bond or an oxygen bridge are also preferred.

Particularly preferred polylene compounds of formula I are:

3,7,11-trimethyl-2,4,10-dodecatrienoic acid ethyl ester;
10,11-epoxy-3,7,11-trimethyl-2,4-dodecadienoic acid ethyl ester;
3,7,11-trimethyl-2,4,10-dodecatrienoic acid propargyl ester;
10,11-epoxy-3,7,11-trimethyl-2,4-dodecadienoic acid propargyl ester;
3,7,11-trimethyl-2,4,10-dodecatrienyl propargyl ether;
10,11-epoxy-3,7,11-trimethyl-2,4-dodecadienyl propargyl ether;
3,7,11-trimethyl-2,4,10-dodecatrienoic acid N-isobutylamide; 10,11-epoxy-3,7,11-trimethyl-2,4-dodecadienoic acid N-isobutylamide;
3,7,11-trimethyl-;b 2,4-dodecadienoic acid ethyl ester;
3,7,11-trimethyl-2,4-dodecadienoic acid proprargyl ester;
3,7,11-trimethyl-2,4-dodecadienyl propargyl ether;
3,7,11-trimethyl-2,4,10-tridecatrienoic acid ethyl ester;
10,11-epoxy-3,7,11-trimethyl-2,4-tridecadienoic acid ethyl ester;
3,7,11-trimethyl-2,4,10-tridecatrienoic acid propargyl ester;
3,7,11-trimethyl-2,4,10-tridecatrienoic acid allyl ester;
10,11-epoxy-3,7.11-trimethyl-2,4-tridecadienoic acid allyl ester;
3,7,11-trimethyl-2,4,10-tridecatrienoic acid N,N-diethylamide;
3,7,11-trimethyl-2,4,10-tridecatrienyl ethyl ester; and
10,11-epoxy-3,7,11-trimethyl-2,4-tridecadienyl ethyl ether as well as the corresponding polyene compounds which also carry a methyl group in the 10-position.

Another compound of formula I is 10,11-epoxy-3,7,11trimethyl-2,4-tridecadienoic acid diethyl amide.

Preferred starting materials in the process provided by the present invention are:

citronellal;
3,7,11-trimethyl-2,4,10-dodecatrienoic acid;
3,7,10,11-tetramethyl-2,4,10-dodecatrienoic acid;
3,7,11-trimethyl-2,4,10-dodecatrien-1-ol;
3,7,10,11-tetramethyl-2,4,10-dodecatrien-1-ol, tetrahydrocitral;
3,7,11-trimethyl-2,4,10-tridecatrienoic acid; and
3,7,11-trimethyl-2,4,10-tridecatrien-1-ol.

In embodiments (a) and (c) of the process provided by the present invention, a carbonyl compound of formulae II or V is reacted with a phosphine oxide of formula III or formula VI respectively to give a corresponding polyene compound of formula I. This reaction is carried out in the presence of a base, preferably in the presence of an inert organic solvent, for example in the presence of sodium hydride in a solvent such as benzene, toluene, dimethylformamide, tetrahydrofuran, dioxan or 1,2-dimethoxyethane, or in the presence of an alkali metal alcoholate in an alcohol, for example in the presence of sodium methylate in methanol. Generally, this reaction is carried out at a temperature of from $-20°$ C. and the boiling point of the solvent, preferably at between 0°C. and room temperature. In a particularly preferred aspect, a carbonyl compound of formula II is, for example, reacted with a phosphine oxide of formula III in the presence of 2 moles of sodium hydride in absolute tetrahydrofuran, excess sodium hydride being destroyed before the working up by the addition of an absolute alkanol.

In embodiments (b) and (d) of the process provided by the present invention, the reaction of a starting material of formula II-A or VII with a phosphorane of formula IV or formula VIII respectively is preferred carried out in the presence of catalytic amounts of organic acid. Any conventional organic acid such as the lower alkane carboxylic acids and aromatic carboxylic acids can be utilized. Among the preferred acids are acetic acid and benzoic acid. Generally, this reaction is carried out in the presence of an inert organic solvent such as benzene, toluene, dimethylformamide, 1,2-dimethoxyethane or dioxan. In carrying out this reaction, temperatures of from about 20° C. to the boiling point of the solvent are generally utilized.

In embodiment (e) of the process provided by the present invention, the reactants of formulae IX and X are dissolved in an inert organic solvent such as, for example, benzene, toluene, dioxan, 1,2-dimethoxyethane or, preferably, tetrahydrofuran, and cooled or warmed with the addition of an aprotic solvent. Among the conventional aprotic solvents, hexamethyl phosphoric acid triamide are particularly preferred. Generally, this reaction is carried out at a temperature of from 0° C. to the boiling point of the solvent employed. A particularly preferred reaction temperature is 70° C. since, at this temperature, the reaction components dissolved in tetrahydrofuran can be heated to reflux. The reaction component which carries the hydroxyl group is converted into an alkali metal salt before the reaction. The conversion of the alcohol into the corresponding alkali metal salt is carried out by conventional procedures such as in an inert solvent by the action of a corresponding base or of an alkali metal; for example, by the action of sodium hydride on the alcohol in tetrahydrofuran as a solvent.

In embodiment (f) of the process provided by the present invention, a polyene compound of formula I-A is epoxidized in an inert solvent with a peracid to give a polyene compound of formula I in which A and B together represent an oxygen bridge. Any conventional method of epoxidizing a double bond can be used in carrying out this procedure. A preferred procedure is carried out by dissolving the compound of formula I-A in an inert organic solvent, especially in a halogenated hydrocarbon such as chloroform or carbon tetrachloride, preferably methylene chloride, and then treating this solution at a temperature of from 0° C. to about 35° C. with a peracid such as, for example, performic acid, peracetic acid, perbenzoic acid, perphthalic acid or pertungstic acid, preferably m-chloroperbenzoic acid.

Another method for carrying out embodiment (f) of the process provided by the present invention comprises first hydrohalogenating a polyene compound of formula I-A to produce a compound of the formula:

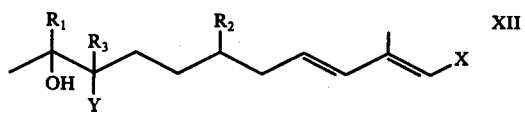

XII wherein Y is a halogen; and $R_1$, $R_2$, $R_3$ and X are as above.

For this hydrohalogenation, the polyene compound of formula I-A is suspended in water and treated with an amount of an inert solvent, for example, dioxan or 1,2-dimethoxyethane, but preferably tetrahydrofuran, such that a homogeneous, concentrated solution results. Where, for example, a polyene compound of formula XII, where Y is bormine, N-bromosuccinimide is introduced portionwise into a solution of the kind mentioned earlier at a temperature between 0° C. to 35° C. Where polyene compounds of formula VII, where Y is chlorine or iodine, are desired, N-chlorosuccinimide or N-iodosuccinimide are used in place of N-bromosuccinimide. A particularly preferred temperature for carrying out this hydrohalogenation is between 0° C. and 5° C.

The halohydrin of formula XII, in the next step, is then converted into an epoxide of formula I-B. For this conversion, the halohydrin is dissolved, in an alkanol, preferably methanol, in the case where X represents an oxymethylene group which can carry a lower alkyl, lower alkenyl or lower alkynyl group and in an ether, preferably diethyl ether, in the case where X represents a carboxylic acid derivative, and treated in the former case with an alkali metal alcoholate, preferably sodium methylate, and in the latter case with a powdered alkali hydroxide, preferably potassium hydroxide. The epoxide of formula I-B is thus obtained in a smooth reaction.

The method described in the preceding paragraph offers the advantage that with esters and ethers only the terminal double bond is epoxidized. When the epoxidation of a polyene compound of formula I-A is carried out using a peracid, the epoxidation does not, in general, lead selectively to the corresponding opoxide, but as a rule there is obtained a mixture of epoxides which can be separated in a manner known per se by chromatography.

According to embodiment (g) of the process provided by the present invention, polyene compounds of formula I-C can be manufactured, for example, by esterifying an acid of formula XI with a compound of formula X in which J represents a hydroxyl group. For this esterification, an acid of formula XI is first converted into a corresponding acid halide by treatment with a halogenating agent such as thionyl chloride, phosphorus trichloride, thionyl bromide or phosphorus oxychloride, preferably thionyl chloride, in an inert solvent, for example, petroleum ether, benzene, hexane, etc., to which there is added an acid-binding agent such as a tertiary amine base. Among the preferred tertiary amine bases are included pyridine, triethylamine, quinoline, etc., particularly pyridine. The acid halide is then reacted with the desired alcohol in an inert organic solvent such as, for example, benzene, toluene, hexane, isooctane, chloroform, carbon tetrachloride or ethylene glycol dimethyl ether in the presence of an acid-binding agent such as, for example, pyridine, triehylamine, quinoline, etc., preferably pyridine, to give the desired ester of formula I-C.

After conversion into the corresponding aciid halide, an acid of formula XI can be converted also in accordance with embodiment (g) of the process provided by the present invention into a polyene compound of formula I-D by treatment with ammonia or an appropriate amine. Any of the conventional methods of converting an organic carboxylic acid into the corresponding amide can be utilized in accordance with this process.

An ester of formula I can be converted in a manner known per se directly into the amide of formula I-D in accordance with embodiment (i) of the process provided by the present invention. Any conventional method of converting as ester to the corresponding amide can be utilized in accordance with this invention.

Further, in accordance with embodiment (h) of the process provided by the present invention, an ester of formula I can be obtained by re-esterification in a manner known per se from an ester manufactured from, for example, an acid of formula XI, i.e., the compound of formula I-C.

The starting materials of formula II where A and B taken together form an oxygen bridge can be prepared by the epoxidation of a compound of formula II-A in the same manner as described earlier for the manufacture of the polyene compounds of formula I from a compound of the formula I-A.

The starting materials of formulae V and VII can be prepared, for example, by reacting a compound of formula II-A with a compound of the formula:

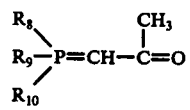

XIII wherein $R_8$, $R_9$ and $R_{10}$ have the significance given earlier;

in the manner described earlier for the Wittig reactions of embodiments (b) and (d). A compound of formula VII obtained where A' and B' taken together are a carbon bond can be eopxidized, if desired, in the manner described earlier in connection with embodiment (f).

Starting materials of formula IX in which the symbol K represents a hydroxyl group can be prepared, for example, by reducing the lower alkyl ester of formula I-C where A and B taken together form a carbon to carbon bond with a lower alkoxy-(lower alkyleneoxy)-alkali-metal-aluminum hydride or an alkali metal aluminum hydride, preferably bis-(methoxy-ethyleneoxy)-sodiumaluminum hydride or lithium aluminum hydride. For this reduction, the lower alkyl ester of formula I-C dissolved according to its solubility properties in a solvent such as, for example, tetrahydrofuran, dioxan, diethyl ether, hexane, toluene or xylene, preferably in benzene in the case where a lower alkoxy-(lower alkyleneoxy)-alkali metal-aluminum hydride is to be used for the reduction and preferably in diethyl ether or tetrahydrofuran in the case where an alkali metal aluminum hydride is to be used for the reduction. The reduction agent is added, preferably in benzene solution. In general, it is sufficient to add the hydride in equimolar amounts, it can, however, sometimes be advantageous to employ about 10–20% excess of hydride. The reduction temperature can vary within wide ranges. The reduction is carried out at a temperature between −70° C. and +80° C. depending on the lower alkyl ester of formula I-C which is employed. In general, a temperature between 0° C. and 20° C. is preferred.

The alcohol obtained by the foregoing reduction can, if desired, be epoxidized and/or converted into a halide of formula IX in which the symbol K represents a chlorine, bromine or iodine atom.

For the conversion of an alcohol of formula IX into a halide of formula IX, the alcohol is dissolved in an inert solvent, for example petroleum ether, benzene, hexane, preferably tetrahydrofuran, and reacted in the presence of an acid-binding agent such as those mentioned hereinbefore. Among the preferred acid-binding agents are included, triethylamine, quinoline, etc., preferably pyridine, with a halogenating agent such as thionyl chloride, phsophorus trichloride, thionyl bromide, phosphorus oxychloride, preferably thionyl chloride.

An acid starting material of formula XI can be prepared, for example, by the alkaline saponification of an ester of formula I-C according to conventional procedures. An acid starting material of formula XI is especially suitable for the manufacture of esters of formula I-C which are difficultly accessible by re-esterification.

The polyene compounds of formula I are obtained according to the present process as a cis/trans isomer mixture. The mixture can be resolved into the isomeric forms; for example, by adsorption on a material with selective activity. The isomer mixture can, for example, be dissolved in an inert organic solvent, for example in hexane, ether or ethyl acetate, and adsorbed on Kieselgel. The isomers adsorbed in various zones can be eluted with one of the aforementioned solvents or mixtures thereof and isolated. In individual cases, the isomer mixture can also be resolved by fractional distillation or by preparative gas chromatography or preparative thin layer chromatography.

The following Examples are illustrative, but not limitative of the invention. In all the examples, the ether utilized was diethyl ether.

EXAMPLE 1

7.45 g of sodium are dissolved in 160 ml of absolute alcohol. This solution is added dropwise at 0° C with stirring within 45 minutes to a mixture of 50 g of citronellal and 85 g of 1-carbethoxy-2-methyl-1-propenyl-diethyl-phosphonate in 480 ml of absolute alcohol. The mixture is subsequently stirred for 2 hours at room temperature. The reaction mixture is poured onto ice and extracted with diethyl ether. The ether phase is washed neutral, dried and evaporated. The crude product is chromatographed on 3 kg of Kieselgel (eluant: 90 percent by volume hexane/10 percent by volume ethyl acetate). There is obtained 3,7,11-trimethyl-2-cis/trans, 4-cis/trans, 10-dodecatrienoic acid ethyl ester of boiling point 97°–98° C/0.018 mmHg (colorless liquid).

EXAMPLE 2

6 g of 3,7,11-trimethyl-2-cis/trans, 4-cis/trans-dodecatrienoic acid ethyl ester are dissolved in 75 ml of methylene chloride and treated portionwise with stirring at 0° C with 5 g of m-chloroperbenzoic acid (ca 80 percent). The mixture is subsequently stirred for a further 1½ hours at 0° C. The reaction mixture is poured onto ice and 1-N aqueous sodium hydroxide and extracted with diethyl ether. The ether phase is washed neutral, dried and evaporated. The product is chromatographed on the 50-fold amount of Kieselgel (eluant: hexane 90 percent by volume/ethyl acetate 20 percent by volume). 10,11-Epoxy-3,7,11-trimethyl-2-cis/trans, 4-cis/trans-dodecadienoic acid ethyl ester is obtained as a colorless oil of boiling point about 135° C/0.01 mmHg (bulb:tube); $n_D^{20} = 1.4907$.

EXAMPLE 3

16 g of 3,7,11-trimethyl-2-cis/trans, 4-cis/trans, 10-dodecatrienoic acid ethyl ester are dissolved in 320 ml of methanol and 80 ml of tetrahydrofuran. The mixture is cooled to 0° C, 34 g of potassium hydroxide in 80 ml of water are added and it is stirred for 18 hours at room temperature. The mixture is poured onto water and extracted with diethyl ether. The water phase is made slightly acidic with 3-N aqueous sulphuric acid and extracted with diethyl ether. The latter ether extract is washed neutral, dried and evaporated. A slightly yellow-colored oil is obtained, which is distilled to give 3,7,11-trimethyl-2-cis/trans, 4-cis/trans, 10-dodecatrienoic acid of boiling point 121° C/0.06 mmHg; $n_D^{20} = 1.5123$.

EXAMPLE 4

6 g of 3,7,11-trimethyl-2-cis/trans, 4-cis/trans, 10-dodecatrienoic acid are dissolved in 50 ml of absolute diethyl ether and 3 ml of pyridine and treated at a temperature between 0° C and 5° C with 4 ml of thionyl chloride (dropping time about 15 minutes). The mixture is subsequently heated for 30 minutes at reflux. After cooling, it is decanted off and the residue is washed out with ether. The solution is evaporated to dryness under anhydrous conditions. The residue is dissolved in 70 ml of absolute diethyl ether and treated at 0° C with 14 g of isobutylamine. After standing for 1 hour at room temperature, it is filtered off. The filtrate is washed with 2-N aqueous hydrochloric acid, then with saturated aqueous sodium bicarbonate solution and finally with water. After drying, the ether phase is evaporated. The crude product is chromatographed on the 100-fold amount of Kieselgel. (Eluant: hexane/ethyl acetate 3:1 parts by volume). There is obtained 3,7,11-trimethyl-2-cis/trans, 4-cis/trans, 10-dodecatrienoic acid N-isobutylamide of boiling point 151° C/0.01 mmHg; $n_D^{20} = 1.5179$.

EXAMPLE 5

3 g of 3,7,11-trimethyl-2-cis/trans, 4-cis/trans, 10-dodecatrienoic acid N-isobutylamide are dissolved in 60 ml of methylene chloride and treated portionwise at a temperature between 0° C and 5° C with 4 g of m-chloroperbenzoic acid (ca 80 percent). The mixture is subsequently stirred for 1½ hours at 0° C. The mixture is poured onto ice and 10 ml of 3-N sodium hydroxide and extracted with diethyl ether. The ether extract is washed neutral, dried and evaporated. The crude product is purified on the 50-fold amount of Kieselgel. (Eluant: hexane/ethyl acetate 3:1 parts by volume). 10,11-Epoxy-3,7,11-trimethyl-2-cis/trans, 4-cis/trans-dodecadienoic acid N-isobutylamide is obtained in the form of a weakly yellow-colored oil: $n_D^{20} = 1.5067$.

EXAMPLE 6

2.9 g of a 50 percent by weight sodium hydride suspension in mineral oil is firstly freed from the oil with absolute hexane and then 30 ml of absolute tetrahydrofuran are added. A solution of 13.5 ml of 3,7,11-trimethyl-2-cis/trans, 4-cis/trans, 10-dodecatrienoic acid in 70 ml of absolute tetrahydrofuran is then slowly added dropwise at 0° C. After refluxing for 30 minutes, the mixture is again cooled to 0° C and 11.8 g of propargyl bromide are added dropwise. After the addition of 30 ml of hexamethyl phosphoric acid triamide, the mixture is heated for 4 hours at reflux. The reaction mixture is poured onto ice-water and extracted with diethyl ether. The ether phase is washed, dried and evaporated. The crude product is purified on the 50-fold amount of Kieselgel. (Eluant: hexane 80 percent by volume/20 percent by volume ethyl acetate). 3,7,11-Trimethyl-2-cis/-trans, 4-cis/trans, 10-dodecatrienoic acid propargyl ester is obtained as a colorless oil of boiling point 125° C/0.02 mmHg (bulb-tube); $n_D^{20} = 1.5122$.

EXAMPLE 7

4.1 g of 3,7,11-trimethyl-2-cis/trans, 4-cis/trans, 10-dodecatrienoic acid propargyl ester are dissolved in 50 ml of methylene chloride and treated portionwise at 0° C with stirring with 3.6 g of m-chloroperbenzoic acid (ca 80 percent). After standing for 1½ hours at 0° C, the mixture is poured onto ice and 1-N-aqueous sodium hydroxide and extracted with diethyl ether. The ether phase is washed, dried and evaporated. The crude product is purified on the 50-fold amount of Kieselgen (eluant: hexane 80 percent by volume/ethyl acetate 20 percent by volume). 10-11-Epoxy-3,7,11-trimethyl-2-cis/-trans, 4-cis/trans-dodecadienoic acid propargyl ester is obtained as a colorless oil boiling point −130° C/0.04 mmHg (bulb-tube); $n_D^{20} = 1.5089$.

EXAMPLE 8

5.1 g of trimethyl-2-cis/trans, 4-cis/trans, 10-dodecatrienoic acid ethyl ester are dissolved in 50 ml of benzene and treated dropwise with stirring at 10° C with 7.5 g of sodium-aluminum-bis(2-methoxyethoxy) hydride (ca 70 percent by weight of the hydride in benzene). After standing for 1 hour at room temperature, there is first added diethyl ether saturated with water and then, slowly, water. The mixture is subsequently filtered and the ether layer is washed neutral, dried and evaporated. The crude oil is distilled in the bulb-tube to give 3,7,11-trimethyl-2-cis/trans, 4-cis/trans, 10-dodecatrien-1-ol of boiling point about 105° C/0.01 mmHg (bulb-tube); $n_D^{20} = 1.5024$.

EXAMPLE 9

800 mg of a 50 percent by weight sodium hydride suspension in mineral oil are firstly freed from the oil by washing with hexane and thereafter overlaid with 15 ml of absolute tetrahydrofuran. A solution of 3.8 g of 3,7,11-trimethyl-2-cis/trans, 4-cis/trans, 10-dodecatrien-1-ol in 15 ml of tetrahydrofuran is then added dropwise at 0° C with stirring. After stirring for 1 hour at room temperature, 3 g of propargyl bromide and 10 ml of hexamethyl phosphoric acid triamide are added at 0° C and the mixture is stirred for 1 ½ hour at 40° C. It is subsequently poured onto ice-water and extracted with diethyl ether. The ether phase is washed, dried and evaporated. The crude product is purified on the 50-fold amount of Kieselgel. (Eluant: 80 percent by volume hexane/ethyl acetate 20 percent by volume). There is obtained 3,7,11-trimethyl-2-dis/trans, 4-cis/trans, 10-dodecatrienyl propargyl ether of boiling point about 115° C/0.01 mmHg (bulb-tube); $n_D^{20} = 1.4983$.

EXAMPLE 10

By the procedure given in Example 1, tetrahydrocitral and 1-carbethoxy-2-methyl-1-propenyl-diethylphosphonate are reacted to produce 3,7,11-trimethyl-2-cis/trans, 4-cis/trans-dodecadienoic acid ethyl ester as a colorless oil of boiling point about 105° C/0.01 mmHg (bulb-tube); $n_D^{25} = 1.4824$.

EXAMPLE 11

By the procedure given in Example 6, 3,7,11-trimethyl-2-cis/trans, 4-cis/trans-dodecadienoic acid is reacted with propargyl bromide to produce 3,7,11-trimethyl-2-cis/trans, 4-cis/trans-dodecadienoic acid propargyl ester, a colorless oil of boiling point 110° C/0.02 mmHg; $n_D^{23} = 1.4970$.

EXAMPLE 12

By the procedure given in Example 3, 3,7,11-trimethyl-2-cis/trans, 4-cis/trans-dodecadienoic acid ethyl ester is converted to 3,7,11-trimethyl-2-cis/trans, 4-cis/-trans-dodecadienoic acid. The thin layer chromatographically and NMR-spectroscopically uniform yellowish oil is used without further purification.

EXAMPLE 13

By the procedure given in Example 9, 3,7,11-trimethyl-2-cis/trans, 4-cis/trans dodecadien-1-ol is converted to 3,7,11-trimethyl-2-cis/trans, 4-cis/trans-dodecadienyl propargyl ether as a colorless oil.

EXAMPLE 14

By the procedure given in Example 8, 3,7,11-trimethyl-2-cis/trans, 4-cis/trans-dodecadienoic acid ethyl ester is converted to 3,7,11-trimethyl-2-cis/trans, 4-cis/-trans-dodecadien-1-ol. Bulb-tube distillation yields a colorless oil of boiling point about 130° C/0.02 mmHg (bulb-tube); $n_D^{23} = 1.4880$.

EXAMPLE 15

By the procedure given in Example 1, 3,7-dimethyl-6-cis/trans-nonenal is reacted with 1-carbethoxy-2-methyl-1-propenyldiethylphosphonate to produce 3,7,11-trimethyl-2-cis/trans, 4-cis/trans, 10-cis-trans-tridecatrienoic acid ethyl ester as a colorless oil of boiling point about 122° C/0.04 mmHg (bulb-tube); $n_D^{24} = 1.4962$.

EXAMPLE 16

129 g of 3,7-dimethyl-2-cis/trans, 6-cis/trans-nonadienal are dissolved in 1.1 liters of ethanol and treated with 3 g of a hydrogenation catalyst (10 percent palladium-on-calcium carbonate). The mixture is stirred at room temperature under 1 atmosphere of hydrogen. The hydrogenation is followed by means of gas chromatography on withdrawn samples. A further 5 g of catalyst (in 2 portions of 3 g and 2 g) are added during the course of the reaction.

The hydrogenation is stopped when no more starting material can be gas chromatographically detected. The reaction product is filtered through CELITE and concentrated on the rotary evaporator.

The oil which accrues is distilled in vacuum. 3,7-dimethyl-6-cis/trans-nonenal is obtained as a colorless oil of boiling point 50° C/0.15 mmHg; $n_D^{24} = 1.4480$.

EXAMPLE 17

By the procedure given in Example 2, 3,7,11-trimethyl-2-cis/trans, 4-cis/trans, 10-cis/trans-tridecatrienoic acid ethyl ester is converted to 10,11-epoxy-3,7,11-trimethyl-2-cis/trans, 4-cis/trans-tridecadienoic acid ethyl ester as a colorless oil of boiling point 138° C/0.03 mmHg (bulb-tube); $n_D^{23} = 1.4787$.

EXAMPLE 18

By the procedure given in Example 6, 3,7,11-trimethyl-2-cis/trans, 4-cis/trans, 10-cis/trans-tridecatrienoic acid is converted to 3,7,11-trimethyl-2-cis/trans, 4-cis/trans, 10-cis/trans-tridecatrienoic acid propargyl ester as a colorless oil of boiling point 140° C/0.05 mmHg (bulb-tube); $n_D^{20} = 1.5088$.

EXAMPLE 19

By the procedure given in Example 3, 3,7,11-trimethyl-2-cis/trans, 4-cis/trans, 10-cis/trans-tridecatrienoic acid ethyl ester is converted to 3,7,11-trimethyl-2-cis/trans, 4-cis/trans, 10-cis/trans-tridecatrienoic acid. The thin layer chromatographically and NMR-spectroscopically uniform yellowish oil was used without further purification.

EXAMPLE 20

10.2 g of 3,7,11-trimethyl-2-cis/trans, 4-cis/trans, 10-cis/trans-tridecatrienoic acid are dissolved in 65 ml of absolute benzene and 3.5 ml of pyridine and then treated at a temperature between 5° C and 10° C with 3.4 ml of thionyl chloride (dropping time ca 15 minutes). The mixture is subsequently stirred for 1 hour at room temperature, then the liquid is decanted off and the residue is washed out with benzene. The solution is evaporated to dryness under anhydrous conditions. The residue is dissolved in 20 ml of absolute benzene and added dropwise at a temperature between 5° C and 10° C to a solution of 3.6 ml of allyl alcohol and 3.5 ml of pyridine in 50 ml of benzene (dropping time ca 30 minutes). After stirring overnight at room temperature, the solution is diluted with ether and washed with 1-N aqueous hydrochloric acid, then with saturated aqueous sodium bicarbonate solution and finally with sodium chloride solution. After drying, the ether phase is evaporated. The crude product is chromatographed on the 30-fold amount of Kieselgel (eluant: hexane/ether 19:1 parts by volume). 3,7,11-Trimethyl-2-cis/trans, 4-cis/trans, 10-cis/trans-tridecatrienoic acid allyl ester is obtained as a colorless oil of boiling point 120° C/0.05 mmHg (bulb-tube); $n_D^{25} = 1.5026$.

EXAMPLE 21

By the procedure in Example 2, 3,7,11-trimethyl-2-cis/trans, 4-cis/trans, 10-cis/trans-tridecatrienoic acid allyl ester is converted to 10, 11-epoxy-3,7,11-trimethyl-2-cis/trans, 4-cis/trans-tridecadienoic acid allyl ester as a colorless oil of boiling point 145° C/0.01 mmHg (bulb-tube); $n_D^{25} = 1.4818$.

EXAMPLE 22

By the procedure given in Example 4, 3,7,11-trimethyl-2-cis/trans, 4-cis/trans, 10-cis/trans-tridecatrienoic acid is reacted with the corresponding amount of diethylamine to produce 3,7,11-trimethyl-2-cis/trans, 4-cis/trans, 10-cis/trans-tridecatrienoic acid diethylamide as a colorless oil of boiling point 140° C/0.02 mmHg (bulb-tube); $n_D^{23} = 1.5057$.

EXAMPLE 23

By the procedure given in Example 9, 3,7,11-trimethyl-2-cis/trans, 4-cis/trans, 10-cis/trans-tridecatrien-1-ol is reacted with the corresponding amount of ethyl bromide to produce 3,7,11-trimethyl-2-cis/trans, 4-cis/trans, 10-cis/trans-tridecatrienyl ethyl ether as a colorless oil of boiling point 117° C/0.025 mmHg (bulb-tube); $n_D^{23} = 1.4751$.

EXAMPLE 24

By the procedure given in Example 8, 3,7,11-2-cis/trans, 4-cis/trans, 10-cis/trans-tridecatrienoic acid ethyl ester is converted to 3,7,11-2-cis/trans, 4-cis/trans, 10-cis/trans-tridecatrien-1-ol. The crude product is purified on the 30-fold amount of Kieselgel (eluant: 80 percent by volume hexane/ether 20 percent by volume). There is obtained a thin layer chromatographically uniform colorless oil, which is used without further purification.

EXAMPLE 25

By the procedure given in Example 2, 3,7,11-trimethyl-2-cis/trans, 4-cis/trans, 10-cis/trans-tridecatrienyl ethyl ether is converted to 10, 11-epoxy-3,7,11-trimethyl-2-cis/trans, 4-cis/trans, 10-cis/trans-tridecadienyl ethyl ether as a colorless oil.

EXAMPLE 26

By the procedure given in Example 1, 3,6,7-trimethyl-6-octenal is reacted with 1-carbethoxy-2-methyl-1-propenyl-diethylphosphonate to produce 3,7,10,11-tetramethyl-2-cis/trans, 4-cis/trans-10-dodecatrienoic acid ethyl ester as a colorless oil of boiling point 115° C/0.025 mmHg; $n_D^{23} = 1.4987$.

EXAMPLE 27

By the procedure given in Example 2, 3,7,10-11-tetramethyl-2-cis/trans, 4-cis/trans-10-dodecatrienoic acid ethyl ester is converted to 10,11-epoxy-3,7,10,11-tetramethyl-2-cis/trans, 4-cis/trans-dodecatrienoic acid ethyl ester as a colorless oil of boiling point 113° C/0.05 mmHg (bulb-tube); $n_D = 1.4930$.

EXAMPLE 28

In a manner analogous to that described in Example 6, from 3,7,10,11-tetramethyl-2-cis/trans, 4-cis/trans-10-dodecatrienoic acid there is obtained 3,7,10-11-tetramethyl-2-cis/trans, 4-cis/trans-10-dodecatrienoic acid propargyl ester as a colorless oil of boiling point 120° C/0.05 mmHg (bulb tube); $n_D^{23} = 1.5127$.

EXAMPLE 29

By the procedure given in Example 3, from 3,7,10,11-tetramethyl-2-cis/trans, 4-cis/trans-10-dodecatrienoic acid ethyl ester is converted to 3,7,10,11-tetramethyl-2-cis/trans, 4-cis/trans-10-dodecatrienoic acid.

The thin layer chromatographically and NMR-spectroscopically uniform yellowish oil was used without further purification.

EXAMPLE 30

By the procedure given in Example 2, from 3,7,10,11-tetramethyl-2-cis/trans, 4-cis/trans-10-dodecatrienoic acid propargyl ester is converted to 10,11-epoxy-3,7,10,11-tetramethyl-2-cis/trans, 4-cis/trans-dodecadienoic acid propargyl ester as a colorless oil.

EXAMPLE 31

3.4 g of 3,7,10-11-tetramethyl-2-cis/trans, 4-cis/trans-10-dodecatrienoic acid are dissolved in 20 ml of absolute ether and 1.2 ml of pyridine and treated at a temperature between 0° C and 5° C with 1.2 ml of thionyl chloride (dropping time about 10 minutes). The mixture is subsequently stirred for 2 hours at room temperature, then the liquid is decanted off and the residue is washed out with diethyl ether. The solution is evaporated to dryness under anhydrous conditions.

The residue is dissolved in 10 ml of ether and this solution is added dropwise with stirring to a cooled solution of 10 ml of concentrated aqueous ammonia solution in such a way that the internal temperature does not rise above 15° C. After the addition, the mixture is stirred for a further 1 hour at room temperature.

It is then diluted with diethyl ether and washed with sodium chloride solution. After drying, the ether phase is evaporated. The crude product is chromatographed on the 30-fold amount of Kieselgel (eluant: hexane/ether 9:1 parts by volume).

3,7,10,11-Tetramethyl-2-cis/trans, 4-cis/trans-10-dodecatrienoic acid amide is obtained as a colorless oil of boiling point 175° C/0.04 mmHg (bulb-tube); $n_D^{23} = 1.5320$, which crystallizes on standing.

EXAMPLE 32

By the procedure given in Example 9, 3,7,10-11-tetramethyl-2-cis/trans, 4-cis/trans-10-dodecatrien-1-ol is converted to 3,7,10-11-tetramethyl-2-cis/trans, 4-cis/-trans-10-dodecatrienyl propargyl ether as a colorless oil of boiling point about 125° C/0.04 mmHg (bulb-tube); $n_D^{24} = 1.4979$.

EXAMPLE 33

By the procedure given in Example 8, 3,7,10-11-tetramethyl-2-cis/trans, 4-cis/trans-10-dodecatrienoic acid ethyl ester is converted to 3,7,10-11-tetramethyl-2-cis/-trans, 4-cis/trans-10-dodecatrien-1-ol. The thin layer chromatographically uniform crude product, a colorless oil, is used without further purification.

EXAMPLE 34

*Dysdercus cingulatus:* Sterilant action.

Filter paper strips of 90 cm² area are uniformly drenched with a solution of the active ingredient in acetone and allowed to dry. For each variant, a plastic beaker is lined with the filter paper and there are placed therein 3-4 pairs each of freshly moulted imagos which are fed with cotton seeds and watered with water. The laying of eggs commences after a few days. The eggs are removed daily and brought into vessels suitable for the hatching of the larvae.

The action of the active ingredient manifests itself in the dying-off of the embryos in the egg or the larvae shortly after hatching (the viability of the larvae is only tested up to the second larval stage).

The results are expressed in percent egg mortality compared with the control.

The dosage is stated in $10^{-x}$g active ingredient/cm² of filter paper, dosage 5 accordingly signifies: $10^{-5}$ g/cm².

| | concentration $10^{-x}$g active ingredient/cm² (dosage) | Sterilant action in percent |
|---|---|---|
| 10,11-epoxy-3,7,11-trimethyl-2,4-dodecadienoic acid ethyl ester (cis/trans mixture) | 5 | 100 |
| | 6 | 100 |
| 3,7,11-trimethyl-2,4,10-dodecatrienoic acid ethyl ester | 5 | 100 |
| | 6 | 79 |

We claim:
1. A compound of the formula:

$$CH_3-\underset{\underset{O}{\diagdown\diagup}}{\overset{R_1}{\underset{|}{C}}}-\overset{R_3}{\underset{|}{C}}-CH_2-CH_2-\overset{R_2}{\underset{|}{CH}}-CH_2-$$

$$-CH=CH-\overset{CH_3}{\underset{|}{C}}=CH-\overset{O}{\overset{\|}{C}}-N\overset{R_4}{\diagdown R_5}$$

wherein $R_1$ and $R_2$ are methyl and ethyl; $R_3$ is hydrogen or methyl; and $R_4$ and $R_5$ are hydrogen or lower alkyl.

2. The compound of claim 1 wherein said compound is 10,11-epoxy-3,7,11-trimethyl-2,4-dodecadienoic acid N-isobutylamide.

3. The compound of claim 1 wherein said compound is 10,11-epoxy-3,7,11-trimethyl-2,4-tridecadienoic acid diethylamide.

* * * * *